United States Patent [19]
Maeda

[11] Patent Number: 5,830,827
[45] Date of Patent: Nov. 3, 1998

[54] GRANULAR HERBICIDAL COMPOSITION COMPRISING FLAZASULFURON AND A SULFOSUCCINATE OR BENZOATE STABILIZER

[75] Inventor: Masaru Maeda, Shiga, Japan

[73] Assignee: Ishihara Sangyo Kaisha, Ltd., Osaka, Japan

[21] Appl. No.: 712,514

[22] Filed: Sep. 13, 1996

[30] Foreign Application Priority Data

Sep. 21, 1995 [JP] Japan .................................. 7-269469

[51] Int. Cl.⁶ ........................... A01N 25/12; A01N 43/40
[52] U.S. Cl. ............................ 504/215; 504/116
[58] Field of Search .................... 504/116, 215

[56] References Cited

U.S. PATENT DOCUMENTS 5,466,693  11/1995  Warrington et al. .................... 514/269

FOREIGN PATENT DOCUMENTS 0462585  6/1991  European Pat. Off. .
0475392  9/1991  European Pat. Off. .
A 5271021  3/1992  Japan .
0184385  9/1990  United Kingdom .

OTHER PUBLICATIONS

CA 125:79418, Nakayama et al, "Stabilized solid agrochemical preparations containing sulfonylureas", JP08104603 (Apr. 23, 1996).

CA 121:151299, Ito et al, "Manufacture of Pesticidal Granules", JP06072801, (Mar. 15, 1994).

Caizi: 127883, Ito et al, "Solid Pesticidal preparations", JP06072803, (Mar. 15, 1994).

Chemical Abstracts, vol. 120, No. 11, Abstract 120:127796 of JP5–271021 1994, "Herbicide Compositions Containing Magnesium Salts".

*Primary Examiner*—S. Mark Clardy
*Attorney, Agent, or Firm*—Sughrue, Mion, Zinn, Macpeak & Seas

[57] ABSTRACT

A granular herbicidal composition which comprises 1-(4,6-dimethoxypyrimidin-2-yl)-3-(3-trifluoromethyl-2-pyridylsulfonyl)urea or a salt thereof as a herbicidal active ingredient, together with a chemical stabilizer and a carrier.

7 Claims, No Drawings

GRANULAR HERBICIDAL COMPOSITION COMPRISING FLAZASULFURON AND A SULFOSUCCINATE OR BENZOATE STABILIZER

FIELD OF THE INVENTION

The present invention relates to a granular herbicidal composition which comprises 1-(4,6-dimethoxypyrimidin-2-yl)-3-(3-trifluoromethyl-2-pyridylsulfonyl)urea (common name: flazasulfuron, hereinafter referred to simply as "Compound A") or a salt thereof as a herbicidal active ingredient, together with a chemical stabilizer and a carrier.

BACKGROUND OF THE INVENTION

JP-A-5-271021 discloses an improved herbicidal composition to which an inorganic magnesium salt is added, the composition comprising Compound A or a salt thereof and at least one compound selected from the group consisting of glufosinate, bialaphos, glyhosate and salts thereof as an active ingredient (the term "JP-A" as used herein means an "unexamined published Japanese patent application"). When the improved herbicidal composition is diluted with water and sprayed, the active ingredient in the spray solution is stabilized, the acidity of the spray solution is improved, and the hygroscopicity of preparations is inhibited by adding the inorganic magnesium salt. That is, JP-A-5-271021 does not disclose or suggest the granular herbicidal composition of the present invention wherein the storage stability of Compound A is enhanced by using a specific chemical stabilizer.

On the other hand, most of herbicides for use in crop lands (e.g., uplands, orchards, mulberry plantations) and non-crop lands (e.g., forests, factory sites, turf fields) are formulations which are diluted with water prior to spraying, such as wettable powders, emulsifiable concentrates, and liquid formulations. During the entire process of weeding with the use of such a herbicide, a considerably long time and much labor are needed for securing and transporting water, preparing a spray solution, and the like. Thus, the longer time and the more labor are required with an increase in the application area in the case of spraying in flat lands as well as in mountains. In order to minimize the labor, the dilution of the herbicide with water itself should be reconsidered.

Accordingly, there have been developed various granular herbicidal compositions such as micro granules without diluting with water. Although formulation of a granular herbicidal composition comprising Compound A as a herbicidal active ingredient is attempted to thereby give an improved granular herbicidal composition, there remained a problem in the storage stability of Compound A in the composition.

SUMMARY OF THE INVENTION

Under these circumstances, the present inventors have conducted extensive studies in order to find an excellent granular herbicidal composition while taking the storage stabilization of Compound A into consideration. As a result, the present invention have been accomplished.

That is, the present invention relates to a granular herbicidal composition which comprises Compound A or a salt thereof as a herbicidal active ingredient, together with a chemical stabilizer and a carrier.

DETAILED DESCRIPTION OF THE INVENTION

Examples of the salt of Compound A used as the herbicidal active ingredient in the granular herbicidal composition of the present invention include a salt of alkali metal (e.g., sodium, potassium), a salt of alkaline earth metal (e.g., magnesium, calcium), a salt of amine (e.g., monomethylamine, monoisopropylamine, dimethylamine, diisopropylamine, triethylamine), and a salt of quaternary ammonium cation (e.g., trimethylethylammonium cation, tetramethylammonium cation).

Examples of the chemical stabilizer for use in the present invention include at least one compound selected from the group consisting of dialkylsulfosuccinates and benzoates. Examples of the salts in the dialkylsulfosuccinates and benzoates include those similar to the above-described salts of Compound A. The chemical stabilizer is preferably a mixture of dialkylsulfosuccinate and benzoate, a sodium dialkylsulfosuccinate, or a sodium benzoate, and more preferably a mixture of sodium dialkylsulfosuccinate and sodium benzoate.

Examples of the carrier for use in the present invention include diatomaceous earth, slaked lime, calcium carbonate, talc, white carbon, bentonite, a mixture of kaolinite and sericite, starch, sodium carbonate, sodium bicarbonate, mirabilite, clay, zeolite, ammonium sulfate, sodium sulfate, and sodium chloride. Among these, talc, bentonite and clay are preferably used. These carriers may be used alone or as a mixture of two or more. For example, a mixture or combination of talc and bentonite, or a mixture or combination of clay and bentonite is preferably used.

If necessary, the granular herbicidal composition of the present invention may further comprise various formulants or herbicidal active ingredients other than Compound A. Next, they will be described below.

The formulants are used for contributing to the improvement in the physical properties of the granular herbicidal composition.

Examples thereof include anionic surfactants, such as a salt of fatty acid, an alkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of a condensate of naphthalene sulfonate with formalin, and a salt of polyacrylic acid;

nonionic surfactants, such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester;

binders, such as starch, dextrin, gum arabic, gelatin, a sodium salt of carboxymethyl cellulose, methyl cellulose, hydroxyethyl cellulose, a sodium lignin sulfonate, a calcium lignin sulfonate, and hydroxypropyl cellulose (preferably a sodium salt of carboxymethyl cellulose, a sodium lignin sulfonate, a calcium lignin sulfonate and hydroxypropyl cellulose);

oil-absorbents, such as white carbon, hydrolyzed starch, clay, talc, diatomaceous earth, an artificially synthesized product of diatomaceous earth and lime, asbestos, a mixture of kaolinite and sericite, calcium silicate, calcium carbonate, calcium carbonate silicate, acid clay, carbon black, graphite, pearlite, alumina, titanium dioxide, basic magnesium carbonate, magnesium silicate aluminate, silica.alumina filler, and magnesium silicate hydrate;

solvents, such as ethers (e.g., dioxane), ketones (e.g., cyclohexanone, methylisobutylketone), fatty acids (e.g., acetic acid, butyric acid), esters (e.g., isopropyl acetate, butyl acetate), nitrogen- or sulfur-containing solvents (e.g., N-methylformamide, N-methylpyrrolidone, dimethylsulfoxide, 1,3-dimethyl-2-imidazolidinone), aliphatic hydrocarbons (e.g., normal paraffin, isoparaffin), and aromatic hydrocarbons (e.g., benzene, alkylbenzene, naphthalene, alkylnaphthalene, diphenyl, phenylxylylethane); and organic acids, such as (anhydrous) citric acid, benzoic acid, and benzenesulfonic acid. These formulants may be used alone or as a mixture of two or more.

The herbicidal active ingredients other than Compound A include the following ones (expressed in common names). They may be used alone or as a mixture of two or more.

(1) Those which are believed to exhibit herbicidal effects as a result of their ability to mimic the activity of endogenous auxin, including phenoxy compounds, such as 2,4-D, MCPA, MCPB, and naproanilide;

aromatic carboxylic acid compounds, such as 2,3,6-TBA, dicamba, and picloram; and others, such as benazolin and quinclorac.

(2) Those which are believed to exhibit herbicidal effects by inhibiting photosystem of plants, including urea compounds, such as diuron, linuron, isoproturon, and metobenzuron;

triazine compounds, such as simazine, atrazine, atratone, simetryn, prometryn, dimethametryn, metribuzin, and terbuthylazine;

uracil compounds, such as bromacil and lenacil;

anilide compounds, such as propanil and cypromid;

carbamate compounds, such as swep and phenmedipham;

hyroxybenzonitrile compounds, such as bromoxynil and ioxynil; and others, such as pyridate and bentazon.

(3) Quaternary ammonium salt compounds such as paraquat and diquat, which are believed to exhibit herbicidal effects by oxygen activation and oxygen reduction.

(4) Those which are believed to exhibit herbicidal effects by inhibiting chlorophyll biosynthesis of plants and abnormally accumulating a photooxidizer of membrane lipids in the plant body, including diphenyl ether compounds, such as nitrofen, chlomethoxyfen, bifenox, acifluorfen-sodium, and fomesafen;

cyclic imide compounds, such as chlorphthalim, flumioxadine, and flumiclorac-pentyl; and others, such as oxadiazon, sulfentrazone, thidiazimin, and ethyl 2-chloro-5-(4-chloro-5-difluoromethoxyl-1-methylpyrazol-3-yl)-4-fluorophenoxyacetate (described in Proceedings of 21st Meeting of Pesticide Science Society of Japan, pp. 70–71).

(5) Those which are believed to exhibit herbicidal effects characterized by the bleaching effect by inhibiting pigment (e.g., carotenoids) biosynthesis of plants, including pyridazinone compounds, such as norflurazon and metflurazon;

pyrazole compounds, such as pyrazolate, pyrazoxyfen, and benzofenap; and others, such as fluridone, flurtamone, diflufenican, methoxyphenone, clomazone, sulcotrione, isoxaflutole, and difenzoquat.

(6) Those which exhibit herbicidal effects specifically to grass weeds, including aryloxyphenoxypropionic acid compounds, such as diclofop-methyl, pyriphenop-sodium, fluazifop-butyl, haloxyfop-methyl, quizalofop-ethyl, and cyhalofop-butyl; and cyclohexanedione compounds, such as alloxydium-sodium, clethodim, sethoxydim, and tralkoxydim.

(7) Those which are believed to exhibit herbicidal effects by inhibiting an amino acid biosynthesis of plants, including sulfonylurea compounds, such as chlorimuron-ethyl, sufometuron-methyl, primisulfuron-methyl, bensulfuron-methyl, chlorsulfuron, metsulfuron-methyl, cinosulfuron, pyrazosulfuron-ethyl, azimsulfuron, rimusulfuron, nicosulfuron, imazosulfuron, cyclosulfamuron, prosulfuron, flupyrsulfuron, trisulfuron-methyl, and halosulfuron-methyl;

triazolopyrimidinesulfoneamide compounds, such as flumetsulam and metosulam;

imidazolinone compounds, such as imazapyr, imazethapyr, imazaquin, imazamox, imazameth, and imazamethabenz;

pyrimidinylsalicyclic acid compounds, such as pyrithiobac-sodium, bispyribac-sodium, and pyriminobac-methyl; and others, such as glyphosate-ammonium, glyphosate-isopropylamine, glufosinate-ammonium, and bialaphos.

(8) Those which are believed to exhibit herbicidal effects by inhibiting cell division of plants, including dinitoroaniline compounds, such as trifluralin, oryzalin, nitralin, and pendimethalin;

organic phosphorus compounds, such as amiprofos-methyl, butamifos, anilofos, and piperophos;

phenylcarbamate compounds, such as chlorpropham and barban;

cumylamine compounds, such as daimuron, cumyluron, and bromobutide; and others, such as asulam and dithiopyr.

(9) Those which are believed to exhibit herbicidal effects by inhibiting protein biosynthesis or lipid biosynthesis of plants, including thiocarbamate compounds, such as EPTC, butylate, molinate, dimepiperate, esprocarb, thiobencarb, and pyributicarb;

chloroacetamide compounds, such as alachlor, butachlor, pretilachlor, metolachlor, thenylchlor, and dimethenamid; and others, such as ethobenzanide, mefenacet, thiafluamide, tridiphane, cafenstrole, oxaziclomefon, and 2-ethyl-2-[2-(3-chlorophenyl)-2,3-epoxypropyl]-indan-1,3-dione (compound described in JP-A-2-304043).

The blending ratio of the components contained in the granular herbicidal composition of the present invention cannot be generally specified because it depends on the kind of the blending components, the blending method, and the like. However, based on 100 parts by weight of the granular herbicidal composition as a whole, the amount of Compound A or a salt thereof is usually from 0.02 to 1.0 parts by weight, preferably from 0.03 to 0.6 parts by weight; the amount of the chemical stabilizer is usually from 0.1 to 10.0 parts by weight, preferably from 0.5 to 7.0 parts by weight; and the amount of the carrier constituting the main of the balance is usually from 50.0 to 99.88 parts by weight, preferably from 60.0 to 99.47 parts by weight. When the granular herbicidal composition further comprises various formulants and other herbicidal active ingredients, the total amount of the formulants is usually from 0.1 to 80.0 parts by weight, preferably from 0.2 to 35.0 parts by weight, and the amount of other herbicidal active ingredients is usually from 0.01 to 30.0 parts by weight, preferably from 0.02 to 15.0 parts by weight. The blending ratio of various formulants which may be optionally used will be described in greater detail. The amount of surfactants is usually from 0.1 to 10.0 parts by weight, preferably from 0.2 to 5.0 parts by weight; the amount of binders is usually from 0.1 to 10.0 parts by weight, preferably from 0.2 to 5.0 parts by weight; the amount of oil-absorbents is usually from 0.1 to 50.0 parts by weight, preferably from 0.2 to 20.0 parts by weight; the amount of solvents is usually from 0.1 to 10.0 parts by weight, preferably from 0.2 to 5.0 parts by weight; the amount of organic acids is usually from 0.1 to 10.0 parts by weight, preferably from 0.1 to 5.0 parts by weight.

The granular herbicidal composition of the present invention can be prepared by a publicly known method, for example, extruding granulation, spray drying granulation, fluidized bed granulation, tumbling granulation or agitation granulation. In the extruding granulation which is one of the preferable embodiments of the present invention, for example, Compound A or a salt thereof, the chemical stabilizer and the carrier are blended together optionally with various formulants and other herbicidal active ingredients (In this step, all of the components may be mixed together at once or arbitrary ones may be first mixed followed by the addition of the remaining ones). Next, the obtained mixture is kneaded with water, preferably after dry grinding. When liquid components are used, they may be added together with water in the kneading step. After the completion of the kneading, the material is granulated by using an extruder, dried by fluidized bed drying, compartment tray drying, and the like, and then sieved to thereby give the granular herbicidal composition.

The granular herbicidal composition of the present invention thus prepared usually has a particle size of 16 to 100 mesh (corresponding to 1,000 to 150 $\mu$m), preferably 22 to 83 mesh (corresponding to 710 to 180 $\mu$m). The particle number of the granular herbicidal composition of the present invention is usually from 2,000 to 30,000, preferably from 3,500 to 10,000, per gram of the granular herbicidal composition. The granular herbicidal composition of the present invention having the particle size and the particle number as defined above suffers from no drift at application and can establish excellent herbicidal effects all over the application area.

The granular herbicidal composition of the present invention is applied directly onto crop lands (for example, uplands, orchards, mulberry plantations) and non-crop lands (for example, forests, factory sites, turf fields) without diluting with water. Thus, it is advantageous in that excellent herbicidal effects can be established all over the application area in a small application dose, compared with the conventional micro granules, without causing any problem of drifting.

Next, preferable embodiments of the granular herbicidal composition of the present invention will be given.

(1) A granular herbicidal composition comprising Compound A or a salt thereof as a herbicidal active ingredient, together with a chemical stabilizer and a carrier.

(2) A granular herbicidal composition comprising Compound A as a herbicidal active ingredient, together with a chemical stabilizer and a carrier.

(3) A granular herbicidal composition as described in the above (1) or (2) which further comprises a binder as a formulant.

(4) A granular herbicidal composition as described in the above (1), (2) or (3) which further comprises other herbicidal active ingredient(s).

(5) A granular herbicidal composition as described in the above (1) or (2) which comprises from 0.02 to 1.0 part by weight of Compound A or a salt thereof, and from 0.1 to 10.0 parts by weight of a chemical stabilizer, each based on 100 parts by weight of the granular herbicidal composition, and the balance mainly comprising a carrier.

(6) A granular herbicidal composition as described in the above (3) which comprises from 0.02 to 1.0 part by weight of Compound A or a salt thereof, from 0.1 to 10.0 parts by weight of a chemical stabilizer, and from 0.1 to 10.0 parts by weight of a binder, each based on 100 parts by weight of the granular herbicidal composition, and the balance mainly comprising a carrier.

(7) A granular herbicidal composition as described in the above (4) which comprises from 0.02 to 1.0 part by weight of Compound A or a salt thereof, from 0.1 to 10.0 parts by weight of a chemical stabilizer, from 0.1 to 10.0 parts by weight of a binder, and from 0.01 to 30.0 parts by weight of other herbicidal active ingredient(s), each based on 100 parts by weight of the granular herbicidal composition, and the balance mainly comprising a carrier.

(8) A granular herbicidal composition as described in the above (1), (2), (3), (4), (5), (6) or (7), wherein the chemical stabilizer is at least one compound selected from the group consisting of dialkylsulfosuccinates and benzoates.

(9) A granular herbicidal composition as described in the above (1), (2), (3), (4), (5), (6) or (7), wherein the chemical stabilizer is Newkalgen EX-70 (trade name) produced by Takemoto Oils and Fats Co., Ltd. (a mixture of sodium dioctylsulfosuccinate with sodium benzoate).

(10) A granular herbicidal composition as described in the above (1) , ( 2) , ( 3), (4 ) , (5), (6), (7), (8) or (9), wherein the carrier is at least one material selected from the group consisting of talc, bentonite and clay.

(11) A granular herbicidal composition as described in the above (3), (4), (6), (7), (8), (9) or (10), wherein the binder is at least one material selected from the group consisting of a sodium salt of carboxymethyl cellulose, a sodium lignin sulfonate, a calcium lignin sulfonate and hydroxypropyl cellulose.

(12) A granular herbicidal composition as described in the above (1), (2), (3), (4), (5), (6), (7), (8), (9), (10) or (11) which has a particle size of 16 to 100 mesh (corresponding to 1,000 to 150 $\mu$m).

(13) A granular herbicidal composition as described in the above (1), (2), (3), (4), (5), (6), (7), (8), (9), (10), (11) or (12) which has 2,000 to 30,000 particles per gram of the granular herbicidal composition.

The present invention is now illustrated in greater detail by way of the following examples, but it should be understood that the present invention is not to be construed as being limited thereto. Unless otherwise indicated, all parts, percents, ratios and the like are by weight.

FORMULATION EXAMPLE 1

| | | |
|---|---|---|
| (1) | Compound A | 0.15 parts |
| (2) | A mixture of sodium dioctylsulfosuccinate and sodium benzoate (Newkalgen EX-70; produced by Takemoto Oils and Fats Co., Ltd.) | 1.5 parts |
| (3) | Bentonite (HODAKA (trade name); produced by HOJUN MINING CO., LTD.) | 10.0 parts |
| (4) | Talc (Talc 3S (trade name); produced by Matsumura Sangyo Co., Ltd.) | 88.35 parts |

The above components were uniformly mixed and dry-ground with a centrifugal pulverizer (screen: 1 mm diameter). The ground matter thus obtained was kneaded with water and granulated with an extruder (Model G-72-100 W; produced by Shin-ei Kikai Seisakusho; screen: 0.6 mm diameter), subjected to fluidized bed drying (at 60° C. for 30 minutes) and then sieved [particle size: 22–83 mesh (corresponding to 710–180 µm)] to thereby give a granular herbicidal composition. This product had 5,100 particles per grain.

FORMULATION EXAMPLE 2 to 6

In accordance with the process described in Formulation Example 1, granular herbicidal compositions were prepared with the use of the components listed in Table 1 described below at the given ratios (parts by weight).

TABLE 1

| | Formulation Ex. No. | | | | |
|---|---|---|---|---|---|
| Component | 2 | 3 | 4 | 5 | 6 |
| Compound A | 0.15 | 0.15 | 0.15 | 0.1 | 0.1 |
| Newkalgen EX-70 | 5.0 | 1.5 | 5.0 | 1.5 | 5.0 |
| Bentonite | 10.0 | 25.0 | 25.0 | 25.0 | 25.0 |
| Talc | 84.85 | 73.35 | 69.85 | 73.4 | 69.9 |
| Particles per g | 5500 | 4700 | 5300 | 5150 | 5160 |

The bentonite and talc given in Table 1 were the same as those employed in Formulation Example 1.

FORMULATION EXAMPLE 7

| | | |
|---|---|---|
| (1) | Compound A | 0.1 parts |
| (2) | Newkalgen EX-70 | 1.5 parts |
| (3) | Bentonite (the same as in Formulation Example 1) | 25.0 parts |
| (4) | Talc (the same as in Formulation Example 1) | 71.4 parts |
| (5) | Calcium lignin sulfonate (SANEKISU C (trade name); produced by Nippon Paper Co., Ltd.) | 2.0 parts |

The above components (1) to (4) were uniformly mixed and dry-ground with the use of a centrifugal pulverizer (screen: 1 mm diameter). The ground matter thus obtained was kneaded with water containing the component (5) and granulated with the same extruder as in Formulation Example 1 (screen: 0.6 mm diameter), subjected to fluidized bed drying (at 60° C. for 30 minutes) and then sieved [particle size: 22–83 mesh (corresponding to 710–180 µm)] to thereby give a granular herbicidal composition. This product had 5,200 particles per gram.

FORMULATION EXAMPLE 8

The procedure of Formulation Example 7 was repeated but varying the amount of talc from 71.4 parts to 72.65 parts and replacing 2.0 parts of SANEKISU C by 0.75 parts of hydroxypropyl cellulose to thereby give a granular herbicidal composition. This product had 5,100 particles per gram.

FORMULATION EXAMPLE 9

| | | |
|---|---|---|
| (1) | Compound A | 0.05 parts |
| (2) | Newkalgen EX-70 | 1.5 parts |
| (3) | Bentonite (the same as in Formulation Example 1) | 15.0 parts |
| (4) | Talc (the same as in Formulation Example 1) | 82.95 parts |
| (5) | Anhydrous citric acid | 0.5 parts |

These components were uniformly mixed and processed in the same manner as in Formulation Example 1 to thereby give a granular herbicidal composition. This product had 6,400 particles per gram.

FORMULATION EXAMPLE 10

The procedure of Formulation Example 9 was repeated but varying the amount of Compound A from 0.05 parts to 0.15 parts and the amount of talc from 82.95 parts to 82.85 parts to thereby give a granular herbicidal composition. This product had 4,800 particles per gram.

FORMULATION EXAMPLE 11

The procedure of Formulation Example 9 was repeated but varying the amount of Compound A from 0.05 parts to 0.1 parts, the amount of bentonite from 15.0 parts to 25.0 parts and the amount of talc from 82.95 parts to 72.9 parts to thereby give a granular herbicidal composition. This product had 5,400 particles per gram.

FORMULATION EXAMPLES 12 to 16

In accordance with the process described in Formulation Example 1 or 7, granular herbicidal compositions are prepared with the use of the components listed in Table 2 described below at the given ratios (parts by weight).

TABLE 2

| | Formulation Example No. | | | | |
|---|---|---|---|---|---|
| Component | 12 | 13 | 14 | 15 | 16 |
| Compound A | 0.02 | 0.3 | 0.3 | 0.1 | 0.3 |
| Newkalgen EX-70 | 0.5 | 10.0 | 10.0 | 1.5 | 1.5 |
| Bentonite | 40.0 | 30.0 | 30.0 | 25.0 | 25.0 |
| Talc | | 59.7 | 48.7 | 73.3 | 72.2 |
| Clay | 59.48 | | | | |
| SANEKISU C | | | 5.0 | | |
| Sodium salt of carboxymethyl cellulose | | | | 0.1 | |
| Laveline FAN | | | | | 1.0 |
| Glufosinate | | | 6.0 | | |
| Particle size: | | | | | |
| (mesh) | 22–100 | 18–83 | 22–83 | 30–100 | 22–83 |
| (µm) | 710–150 | 850–180 | 710–180 | 500–150 | 710–180 |
| Particles per gram | 4000–7000 | 3000–5000 | 4000–6000 | 7000–9000 | 4000–6000 |

"Laveline FAN (trade name)" given in Table 2 is a product which comprises a condensate of sodium naphthalenesulfonate and formalin is produced by Dai-Ichi Kogyo Seiyaku Co., Ltd.

FORMULATION EXAMPLE 17

| | | |
|---|---|---|
| (1) | Compound A | 0.1 parts |
| (2) | Newkalgen EX-70 | 10.0 parts |
| (3) | Bentonite (the same as in Formulation Example 1) | 25.0 parts |
| (4) | Talc (the same as in Formulation Example 1) | 64.9 parts |

These components were uniformly mixed and processed in the same manner as in Formulation Example 1 to thereby give a granular herbicidal composition. This product has 4,000 to 6,000 particles per gram.

FORMULATION EXAMPLE 18

| | | |
|---|---|---|
| (1) | Compound A | 0.1 parts |
| (2) | Sodium dioctylsulfosuccinate (GEROPON SDS (trade name); produced by Rhone-poulenc) | 1.5 parts |
| (3) | Bentonite (the same as in Formulation Example 1) | 25.0 parts |
| (4) | Talc (the same as in Formulation Example 1) | 73.4 parts |

These components are uniformly mixed and processed in the same manner as in Formulation Example 1 to thereby give a granular herbicidal composition. This product has 4,000 to 6,000 particles per gram.

FORMULATION EXAMPLE 19

The procedure of Formulation Example 18 is repeated but varying the amount of GEROPON SDS from 1.5 parts to 5.0 parts and the amount of talc from 73.4 parts to 69.9 parts to thereby give a granular herbicidal composition. This product has 4,000 to 6,000 particles per gram.

COMPARATIVE FORMULATION EXAMPLE 1

| | | |
|---|---|---|
| (1) | Compound A | 0.1 parts |
| (2) | Bentonite (the same as in Formulation Example 1) | 25.0 parts |
| (3) | Talc (the same as in Formulation Example 1) | 74.9 parts |

These components were uniformly mixed and processed in the same manner as in Formulation Example 1 to thereby give a granular herbicidal composition. This product had 5,400 particles per gram.

COMPARATIVE FORMULATION EXAMPLE 2

| | | |
|---|---|---|
| (1) | Compound A | 0.15 parts |
| (2) | Bentonite (the same as in Formulation Example 1) | 26.5 parts |
| (3) | Talc (the same as in Formulation Example 1) | 73.35 parts |

These components were uniformly mixed and processed in the same manner as in Formulation Example 1 to thereby give a granular herbicidal composition. This product had 5,200 particles per gram.

TEST EXAMPLE 1

Decomposition Rate of Compound A:

Fifty grams of the granular herbicidal compositions obtained in Formulation Examples 1 to 11 and Comparative Formulation Examples 1 and 2 were each introduced into a glass container provided with a stopper and subjected to an accelerated storage stability test at a constant temperature of 50° C. for 1 month. After predetermined period, the decomposition rate of Compound A was determined by HPLC. Table 3 shows the results.

TABLE 3

| Formulation Example No. | Decomposition Rate (%) of Compound A | |
|---|---|---|
| | After 2 Weeks | After 1 Month |
| 1 | 1.8 | 5.3 |
| 2 | 0.5 | −0.3 |
| 3 | 2.5 | 0.3 |
| 4 | 2.4 | 0.0 |
| 5 | 2.5 | 4.1 |
| 6 | 1.7 | −0.6 |
| 7 | −2.6 | 3.8 |
| 8 | 4.3 | 1.8 |
| 9 | 1.9 | 1.6 |
| 10 | 2.5 | 3.8 |
| 11 | −0.5 | 2.7 |
| Comp. Ex. 1 | 60.0 | — |
| Comp. Ex. 2 | 62.5 | 79.3 |

The results in Table 3 show that the granular herbicidal compositions of the present invention (formulation Examples 1 to 11) containing chemical stabilizers are obviously superior in the storage stability to those free from any chemical stabilizer (Comparative Formulation Examples 1 and 2).

TEST EXAMPLE 2

Decomposition Rate of Compound A:

One hundred grams of the granular herbicidal composition obtained in Formulation Example 17 was introduced into a glass container provided with a stopper and subjected to an accelerated storage stability test at a constant temperature of 40° C. for 3 months. After 3 months, the decomposition rate of Compound A determined by HPLC was 1.6%, which indicated that this product had a remarkably high storage stability similar to the results of Test Example 1.

While the invention has been described in detail and with reference to specific embodiments thereof, it will be apparent to one skilled in the art that various changes and modifications can be made therein without departing from the spirit and scope thereof.

What is claimed is:

1. A granular herbicidal composition which comprises 1-(4,6-dimethoxypyrimidin-2-yl)-3-(3-trifluoromethyl-2-pyridylsulfonyl)urea or a salt thereof as a herbicidal active ingredient, together with a chemical stabilizer and a carriers wherein the granular composition has a particle size of from 16 to 100 mesh corresponding to from 1,000 to 150 μm.

2. The granular herbicidal composition as claimed in claim 1, wherein said chemical stabilizer is at least one compound selected from the group consisting of dialkylsulfosuccinates and benzoates.

3. A granular herbicidal composition which comprises from 0.02 to 1.0 part by weight of 1-(4,6- dimethoxypyrimidin-2-yl)-3-(3-trifluoromethyl-2-pyridylsulfonyl)urea or a salt thereof as a herbicidal active ingredient, and from 0.1 to 10.0 parts by weight of a chemical stabilizer, each based on 100 parts by weight of said granular herbicidal composition, and the balance comprising a carrier wherein the granular composition has a particle size of from 16 to 100 mesh corresponding to from 1,000 to 150 μm.

4. The granular herbicidal composition as claimed in claim 3, wherein said chemical stabilizer is at least one compound selected from the group consisting of dialkylsulfosuccinates and benzoates.

5. The granular herbicidal composition as claimed in claim 3, which further comprises from 0.1 to 80.0 parts by weight of a formulant.

6. The granular herbicidal composition as claimed in claim 3, which further comprises from 0.01 to 30.0 parts by weight of other herbicidal active ingredient.

7. The granular herbicidal composition as claimed in claim 3, which further comprises from 0.1 to 80.0 parts by weight of a formulant and from 0.01 to 30.0 parts by weight of other herbicidal active ingredient.

* * * * *